US009566002B2

(12) United States Patent
Nakahara et al.

(10) Patent No.: US 9,566,002 B2
(45) Date of Patent: Feb. 14, 2017

(54) IMAGE PROCESSING APPARATUS, IMAGE PROCESSING METHOD, AND PROGRAM

(71) Applicant: CANON KABUSHIKI KAISHA, Tokyo (JP)

(72) Inventors: Yasuhiro Nakahara, Kawasaki (JP); Shigeaki Ono, Tokyo (JP); Yukio Sakagawa, Tokyo (JP); Hiroki Uchida, Tokyo (JP)

(73) Assignee: CANON KABUSHIKI KAISHA, Tokyo (JP)

(*) Notice: Subject to any disclaimer, the term of this patent is extended or adjusted under 35 U.S.C. 154(b) by 756 days.

(21) Appl. No.: 13/746,658

(22) Filed: Jan. 22, 2013

(65) Prior Publication Data

US 2013/0188141 A1    Jul. 25, 2013

(30) Foreign Application Priority Data

Jan. 25, 2012   (JP) ................................ 2012-013251
Aug. 30, 2012   (JP) ................................ 2012-190603

(51) Int. Cl.
*A61B 3/14*     (2006.01)
*A61B 3/10*     (2006.01)
*A61B 3/00*     (2006.01)
*G06T 7/00*     (2006.01)

(52) U.S. Cl.
CPC .. *A61B 3/14* (2013.01); *G06T 7/00* (2013.01); *G06T 7/0012* (2013.01); *G06T 2207/10101* (2013.01); *G06T 2207/30041* (2013.01)

(58) Field of Classification Search
CPC ........... A61B 3/103; A61B 3/14; A61B 3/152; A61B 3/1225; A61B 3/024; A61B 3/1015
(Continued)

(56) References Cited

U.S. PATENT DOCUMENTS 8,801,187 B1 *   8/2014   Knighton et al. ............. 351/246
8,803,964 B2 *   8/2014   Wanda et al. .................. 348/78
(Continued)

FOREIGN PATENT DOCUMENTS

CN      1939208 A     4/2007
CN    101040776 A     9/2007
(Continued)

OTHER PUBLICATIONS

Chinese Office Action issued in corresponding application No. 201310030181.8 dated Aug. 4, 2015.
(Continued)

*Primary Examiner* — Dawayne A Pinkney
(74) *Attorney, Agent, or Firm* — Carter, DeLuca, Farrell & Schmidt, LLP

(57) ABSTRACT

To ensure display of a region of interest on a fundus image and a tomographic image of an eye to be inspected in a correspondence manner, an apparatus for processing images of an eye to be inspected includes: a unit that acquires a fundus image of an eye to be inspected; a unit that designates an arbitrary point on the fundus image; a unit that acquires a tomographic image of the eye to be inspected; a unit that calculates a point on the tomographic image corresponding to the arbitrary point; and a unit that converts a coordinate system for displaying the tomographic image and the fundus image in association with each other on the basis of positions of the arbitrary point and the corresponding point.

17 Claims, 12 Drawing Sheets

(58) Field of Classification Search
USPC ....... 351/206, 200, 205, 208, 209, 210, 221, 351/222, 246
See application file for complete search history.

(56) References Cited

U.S. PATENT DOCUMENTS

| | | | |
|---|---|---|---|
| 2007/0177103 A1* | 8/2007 | Migliaccio et al. | 351/206 |
| 2007/0236660 A1 | 10/2007 | Fukuma et al. | |
| 2012/0002164 A1* | 1/2012 | Yamamoto | A61B 3/102 351/206 |
| 2012/0281235 A1* | 11/2012 | Murata et al. | 356/479 |

FOREIGN PATENT DOCUMENTS

| | | | |
|---|---|---|---|
| CN | 101040777 A | | 9/2007 |
| CN | 101204318 A | | 6/2008 |
| JP | 2007-117714 A | | 5/2007 |
| JP | 2008154939 A | | 7/2008 |
| JP | 2010240068 A | * | 10/2010 |
| JP | 2011024842 A | | 2/2011 |
| JP | 2011-505926 A | | 3/2011 |
| JP | 2011-110158 A | | 6/2011 |
| WO | 2009073970 A1 | | 6/2009 |

OTHER PUBLICATIONS

Japanese Office Action issued on May 17, 2016 in corresponding Japanese Patent Application No. 2012190603 with English translation, 4 pages.
Korean Office Action issued on May 15, 2015 in corresponding Korean Patent Application No. 10-2013-0008032 with English translation, 6 pages.

* cited by examiner

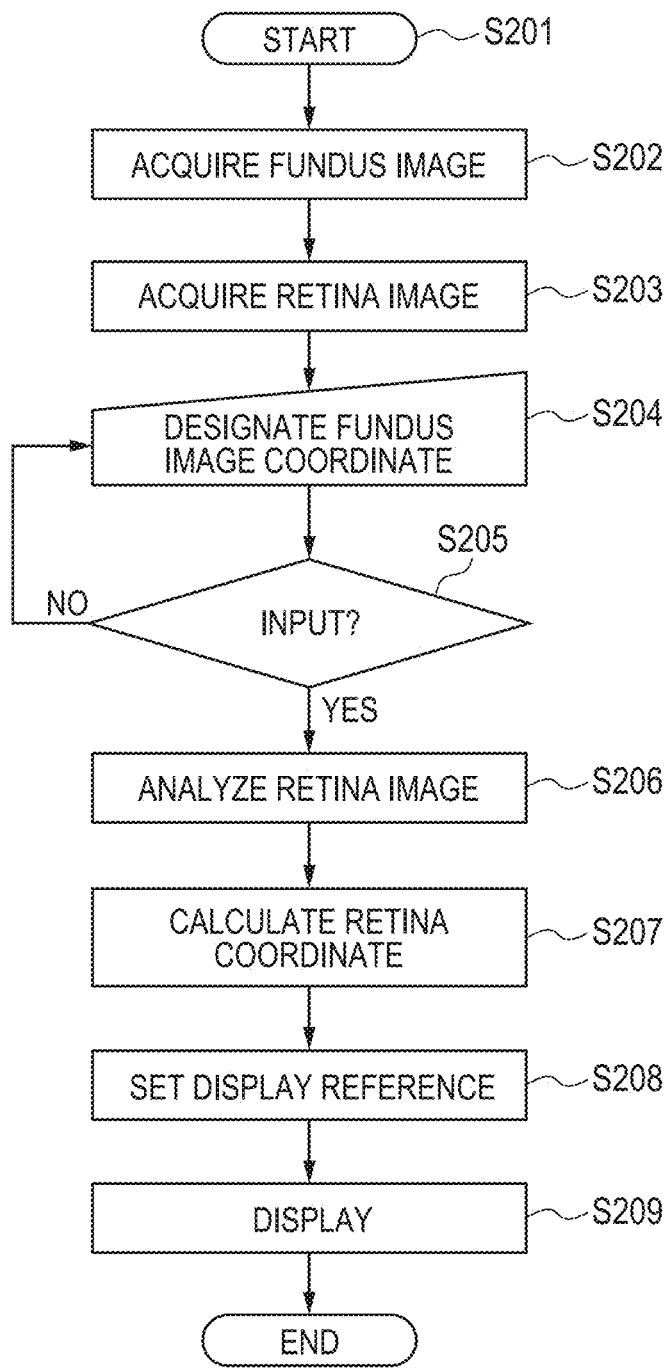

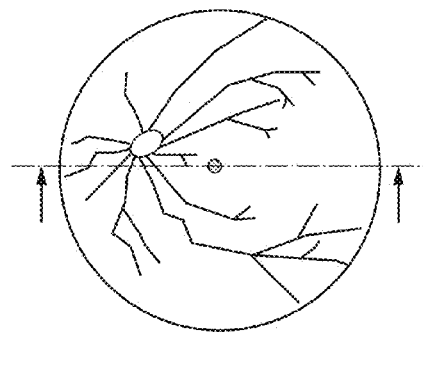
FIG. 7A
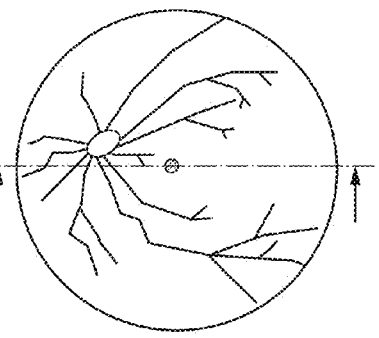
FIG. 7B
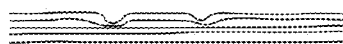

FIG. 13A  FIG. 13B  FIG. 13C
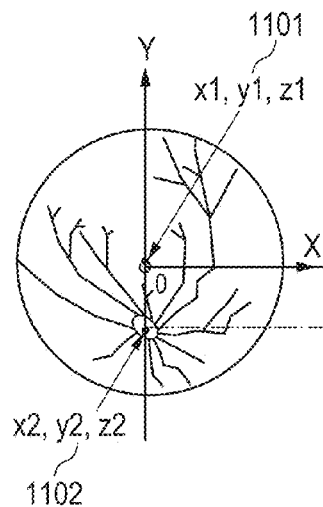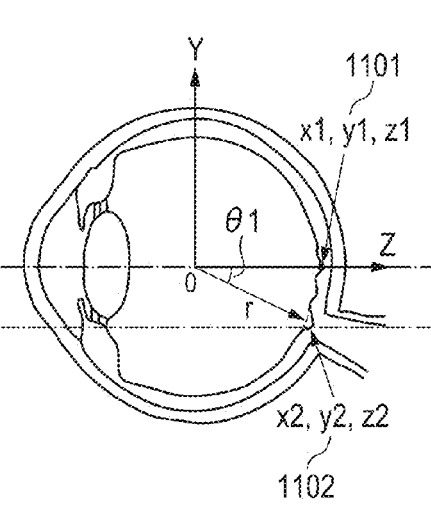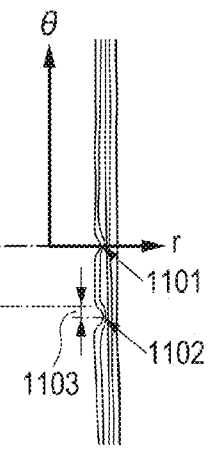
FIG. 14A  FIG. 14B  FIG. 14C
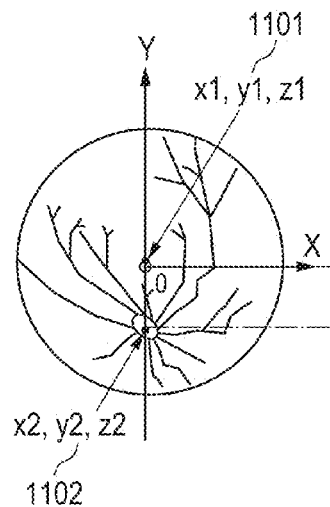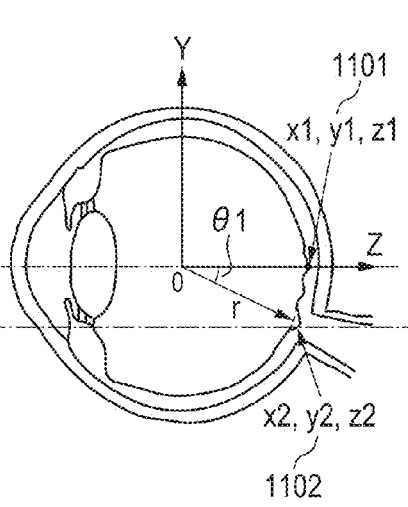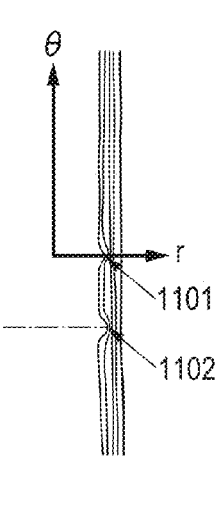

IMAGE PROCESSING APPARATUS, IMAGE PROCESSING METHOD, AND PROGRAM

BACKGROUND OF THE INVENTION

Field of the Invention

The present invention relates to an image processing technology for assisting image processing on images of an eye, and more particularly, to an image processing apparatus, an image processing method, and a program for performing image processing using a tomographic image of an eye.

Description of the Related Art

An ophthalmic tomographic image photographing device such as an optical coherence tomography (OCT) device enables three-dimensional observation of an internal state of a retina. In recent years, this ophthalmic tomographic image photographing device has become popular for its capability of appropriately diagnosing diseases. The amount of OCT tomographic information is huge, and hence it is very inefficient to check the tomographic information piece by piece. To relieve the burden of doctors on OCT-based diagnosis, therefore, there is a demand to establish a computer-aided diagnosis (CAD) technology. For example, Japanese Patent Application Laid-Open No. 2011-110158 describes that characteristic amounts on a fundus image are detected at two points thereof, a reference coordinate system for a projection image is determined on the basis of the two points, and the reference coordinate system is converted to a display coordinate system to display the projection image corresponding to the display coordinate system. Japanese Patent Application Laid-Open No. 2011-110158 proposes a scheme of displaying OCT analysis results in accordance with the display coordinate system.

However, Japanese Patent Application Laid-Open No. 2011-110158 fails to describe processing that is performed in displaying a fundus image and a tomographic image. In general, a tomographic image is expanded and displayed two-dimensionally. When a tomographic image and a fundus image are displayed with a single corresponding point taken as a reference, therefore, the tomographic image and the fundus image match with each other at the origin of the reference coordinate system, but as the distance from the origin of the reference coordinate system is longer, the deviation amount becomes larger. This phenomenon is described referring to schematic diagrams of FIGS. 16A to 16C. FIG. 16A illustrates a fundus image. An arbitrary point 1401 lies on a line extending vertically on the fundus image and passing nearly through the center of the fundus image. An arbitrary point 1402 lies in a macula present on the line. An arbitrary point 1403 is a point on a papilla present on the line. A distance 1404 and a distance 1405 are vertical distances from the arbitrary point 1402 to the arbitrary point 1401 and from the arbitrary point 1402 to the arbitrary point 1403, respectively. FIG. 16B illustrates the cross section of an eye corresponding to the line containing points 1401, 1402 and 1403 at the fundus. FIG. 16C illustrates a tomographic image acquired by OCT-based measurement of the same vertical line. The OCT tomographic image is normally expanded and displayed two-dimensionally with the arbitrary point 1402 as the reference point, that is, the origin. A distance 1406 represents a deviation amount of the actual arbitrary point 1401 on the tomographic image from the arbitrary point 1401 on the fundus image. A distance 1407 represents a deviation amount of the actual arbitrary point 1403 on the tomographic image from the arbitrary point 1403 on the fundus image. As the distances 1404 and 1405 from the display reference point are longer, the deviation between the fundus image and the tomographic image is greater.

When a point of interest (e.g., point which is suspected to be a lesion) is other than the reference point, therefore, an inspector carries out diagnosis by referring to a screen in which the tomographic image and the fundus image do not match with each other. This makes it difficult to support diagnosis of a variety of diseases, and hinders prompt diagnosis.

SUMMARY OF THE INVENTION

The present invention has been made to overcome the above-mentioned problem.

In order to solve the above-mentioned problem, according to an exemplary embodiment of the present invention, there is provided an image processing apparatus, including: a unit that acquires a fundus image of an eye to be inspected; a unit that designates two arbitrary points on the fundus image; a unit that calculates a vector formed between the two arbitrary points; a unit that calculates a coordinate system with the vector being set as one axis and one of the two arbitrary points being set as an origin; a unit that acquires a tomographic image of the eye to be inspected; a unit that matches the origin of the coordinate system with an arbitrary point on the tomographic image corresponding to the origin; a unit that calculates a deviation amount between a position of one of the two arbitrary points on the fundus image, which is not subjected to matching, and a position of a corresponding arbitrary point on the tomographic image; and a unit that converts the tomographic image on the basis of the deviation amount so that the two arbitrary points on the fundus image match with points on the tomographic image which respectively correspond to the two arbitrary points.

In order to solve the above-mentioned problem, according to an exemplary embodiment of the present invention, there is provided an image processing method, including: acquiring a fundus image of an eye to be inspected; designating an arbitrary point on the fundus image; acquiring a tomographic image of the eye to be inspected; calculating a point on the tomographic image corresponding to the arbitrary point; and converting a coordinate system for displaying the tomographic image and the fundus image in association with each other on the basis of positions of the arbitrary point and the corresponding point.

According to another exemplary embodiment of the present invention, there is provided an image processing method, including: acquiring a fundus image of an eye to be inspected; designating two arbitrary points on the fundus image; calculating a vector formed between the two arbitrary points; calculating a coordinate system with the vector being set as one axis and one of the two arbitrary points being set as an origin; acquiring a tomographic image of the eye to be inspected; matching the origin of the coordinate system with an arbitrary point on the tomographic image corresponding to the origin; calculating a deviation amount between a position of one of the two arbitrary points on the fundus image, which is not subjected to matching, and a position of a corresponding arbitrary point on the tomographic image; and converting the tomographic image on the basis of the deviation amount so that the two arbitrary points on the fundus image match with points on the tomographic image which respectively correspond to the two arbitrary points.

The image processing apparatus, the image processing method, and the program according to the present invention are desired to provide the following effect.

Through execution of the image processing according to the present invention, a base point at which a tomographic image and a fundus image match with each other can be changed in accordance with a region of interest (e.g., suspected lesion) so that a variety of diseases can be diagnosed promptly.

Further features of the present invention will become apparent from the following description of exemplary embodiments with reference to the attached drawings.

BRIEF DESCRIPTION OF THE DRAWINGS

FIG. 2 is a flowchart illustrating the program flow of image processing according to the first embodiment of the present invention.

FIGS. 7A and 7B are diagrams exemplifying a case where images displayed in the manner of FIGS. 6A and 6B are mirror-reversed.

FIGS. 13A, 13B and 13C are diagrams illustrating an operation for retina image analysis and calculation of retina coordinates which are carried out in the image processing according to the third embodiment.

FIGS. 14A, 14B and 14C are diagrams illustrating an operation for the calculation of retina coordinates and setting of a display reference which are carried out in the image processing according to the third embodiment.

DESCRIPTION OF THE EMBODIMENTS

Exemplary embodiments of the present invention are described below.

First Embodiment

Figure 1:
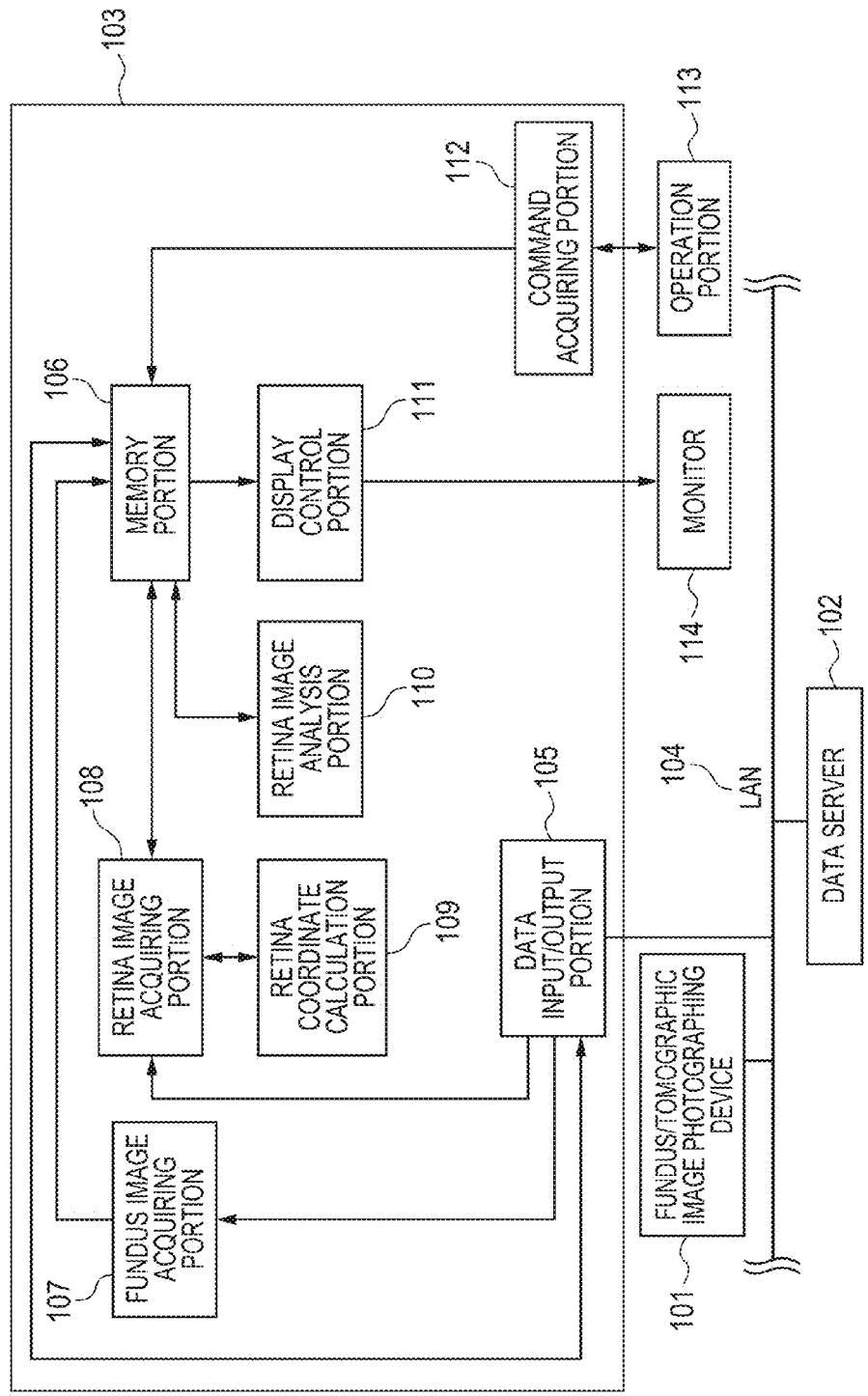
FIG. 1 is a block diagram illustrating the configuration of an image processing apparatus according to a first embodiment of the present invention.

The configuration of an image processing apparatus, image processing, and a program according to a first embodiment of the present invention are described referring to FIGS. 1 and 2. FIG. 1 is a block diagram illustrating the image processing apparatus according to the first embodiment, which is configured to actually carry out image processing.

A fundus/tomographic image photographing device 101 according to the first embodiment picks up a fundus image and a tomographic image of an eye. The fundus image is picked up by a structure such as a solid-state image pickup device like a charge coupled device image sensor (CCD) (not shown), or a scanning laser ophthalmoscope (SLO). According to the first embodiment, the tomographic image of an eye is acquired by, for example, a time-domain OCT device or a Fourier-domain OCT device. According to the configuration, the optical path of an eye to be inspected (not shown) is split by a half mirror or the like to allow simultaneous observation and analysis of the fundus image and the tomographic image of the eye, and the fundus image, tomographic image, and the result of the analysis are formed into data.

A data server 102 holds data on the fundus image and tomographic image of the eye to be inspected, and the characteristics of the images of the eye to be inspected. That is, the data server 102 stores the fundus image or tomographic image of the eye to be inspected which is output from the fundus/tomographic image photographing device 101, the analysis result output from an image processing portion 103, and the fundus and retina reference coordinate systems. The data server 102 transmits previous data on the eye to be inspected and data on a normal eye to the image processing portion 103 in response to a request from the image processing portion 103.

The image processing portion 103 includes a data input/output portion 105, a fundus image acquiring portion 109A retina image acquiring portion 1010A retina coordinate calculation portion 1011A memory portion 106, a retina image analysis portion 110, a display control portion 113 And a command acquiring portion 112. The image processing portion 103 is connected to the data server 102 and the fundus/tomographic image photographing device 101 over a local area network (LAN) 104. The image processing portion 103 may be connected to the data server 102 and the fundus/tomographic image photographing device 101 via a USB, IEEE 1394, or the like.

Figure 3A:
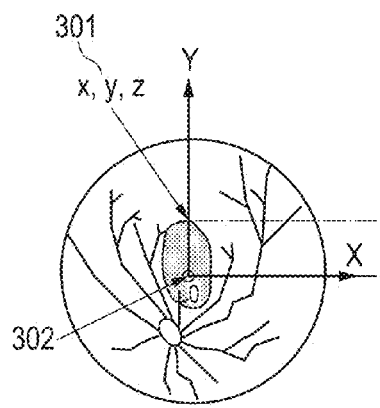
FIGS. 3A, 3B and 3C are diagrams illustrating an operation for retina image analysis and calculation of retina coordinates which are carried out in the image processing according to the first embodiment.
Figure 3B:
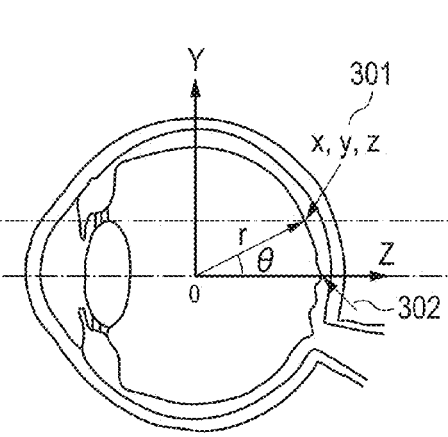

The retina image analysis portion 110 determines the coordinates of a radius r and a center point 0 of an eyeball in a three-dimensional tomographic image in FIG. 3B. The origin 302 is aligned with the centre 0 of the eyeball. Next, coordinates (x,y,z) on a three-dimensional tomographic image of a designated point 301 are calculated from x and y coordinate values (designated point on the fundus) of the designated point 301, which corresponds to a characteristic point according to the present invention, in a fundus image in FIG. 3A. The data input/output portion 105 serves as an interface portion for data input/output between the image processing portion 103 and the data server 102 or the fundus/tomographic image photographing device 101. The fundus image acquiring portion 109 Acquires fundus image data transmitted from the fundus/tomographic image photographing device 101 to the data input/output portion 105 over the LAN 104. Then, the fundus image acquiring portion 109 analyzes the characteristic point of the fundus and performs the conversion of the coordinates to a display coordinate system, and sends obtained result data to the memory portion 106. According to the present invention, the fundus/tomographic image photographing device 101, the fundus image acquiring portion 107, etc., which acquire the fundus image, correspond to a means or unit for acquiring the fundus image of an eye to be inspected. Further, according to the present invention, the fundus/tomographic image photographing device 101, the retina image acquiring portion 108, etc., which acquire the tomographic image, correspond to a means or unit for acquiring the tomographic image of the eye to be inspected.

An operation portion 113 is a pointing device usable to point out an arbitrary point which may be a lesion of the fundus image displayed on a monitor 114 (which is described later). That is, the operation portion 113 serves as a unit that is used to designate an arbitrary point or two arbitrary points on the fundus image according to the present invention. An example of the operation portion 113 is a touch panel installed on the monitor 114 or a mouse, but the present invention is not limited thereto. The operation portion 113 may be any device which can designate an arbitrary position or an arbitrary point of the fundus image on the monitor 114. When the operation portion 113 inputs an arbitrary point on the fundus, the command acquiring portion 114 Converts the arbitrary point input on the monitor 114 to the coordinates of the fundus image, and sends the coordinate data to the memory portion 106.

The fundus image and the tomographic image acquired by the fundus/tomographic image photographing device 101, and the image information analyzed by the image processing portion 103 are converted to the display coordinate system to be displayed on the monitor 114. The retina image acquiring portion 1010 Acquires the tomographic image data of the eye to be inspected transmitted to the data input/output portion 105 over the LAN 104 from the fundus/tomographic image photographing device 101. The retina coordinate calculation portion 109 performs a process of calculating three-dimensional data of a characteristic point or an arbitrary point to be diagnosed, radius information of the eye, etc. from the tomographic image data acquired by the retina image acquiring portion 1010 And converting the calculated information to the display coordinate system. The tomographic image data converted to the display coordinate system is transferred to the memory portion 106.

The memory portion 106 also serves as a processing portion to associate the coordinates of the fundus image with those of the tomographic image. The memory portion 106 causes a designated arbitrary point of the fundus image and a position on the tomographic image which corresponds to the arbitrary point to be displayed on the monitor 114 in association with each other.

Figure 3C:
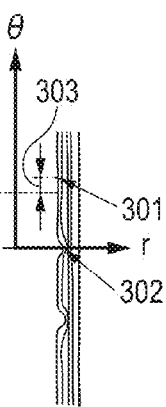

FIG. 2 illustrates the flow of a program which is executed by the image processing portion 103 and some other components described above. Step S201 is the start of the flow of the image processing program. In Step S202, the fundus/tomographic image photographing device 101 acquires the fundus image of an eye to be inspected. Then, a two-dimensional XY coordinate system is calculated with a macula portion 302 of FIGS. 3A to 3C as the origin, and the two-dimensional XY coordinate system is sent to the memory portion 106 with the origin as the origin of the reference coordinates. Those processes are executed by the fundus image acquiring portion 107.

Further, in Step S203, the fundus/tomographic image photographing device 101 acquires the tomographic image of the eye to be inspected. In Step S204, the coordinates of a portion on the fundus image which needs to be diagnosed are designated as an arbitrary point. This operation is executed as designation or the like of the arbitrary point by the above-mentioned operation portion 113.

In Step S205, it is determined whether or not the coordinates of the arbitrary point on the fundus image are input. When there is not any input of the coordinates, the flow returns to Step S204 to wait for an input of the coordinates. When the coordinates are input, the flow proceeds to next Step S206. In Step S206, three-dimensional coordinates of the previously determined origin on the retina in the tomographic image to be described later are calculated during analysis of the fundus image. This process is described referring to FIGS. 3A to 3C. The radius r of the eyeball and the center point O in the eyeball in the cross-sectional view illustrated in FIG. 3B are determined, and correspondence between the above-mentioned origin and the center point in the three-dimensional coordinate system to be set for the tomographic image is made. Further, reference coordinates (x,y,z) which are matched with the XY coordinates set to the fundus image are calculated. The above-mentioned process of calculating a point on the tomographic image which corresponds to an arbitrary point on the fundus image according to the present invention is executed by the retina image analysis portion 110 and other components that constitute a means or unit for calculating the corresponding point. The center point O can be determined from the curvature on the tomographic image.

In Step S207, the three-dimensional coordinates of an arbitrary point 301 on the tomographic image illustrated in FIG. 3B are calculated from the calculated reference coordinates on the fundus. Next, an expansion distance (re) on the retina from the origin 302 to the arbitrary point 301 on the tomographic image in the three-dimensional reference coordinates (x,y,z) is determined. Then, the difference between the determined expansion distance and the distance from the origin 302 to 301 in the Y-axial direction in the XY coordinate system set for the fundus image at the arbitrary point 302 is calculated. The determined difference represents a deviation amount 303 when an arbitrary point on the fundus image is displayed in association with the arbitrary point on the tomographic image corresponding to the former arbitrary point.

Figure 4A:
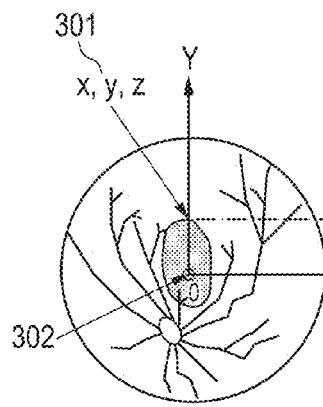
FIGS. 4A, 4B and 4C are diagrams illustrating an operation for the calculation of retina coordinates and setting of a display reference which are carried out in the image processing according to the first embodiment.
Figure 4B:
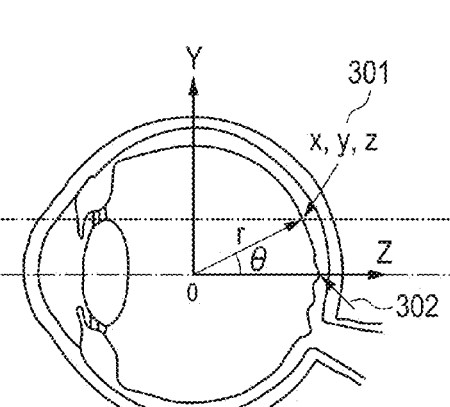
Figure 4C:
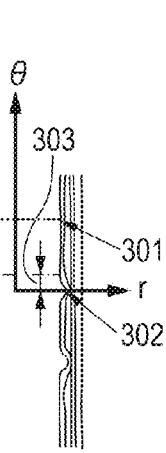

In Step S208, in consideration of this deviation amount 303, the coordinates of the three-dimensional coordinate system are converted to the display coordinate system in such a way that the coordinates of the designated arbitrary point 301 on the fundus image match with the coordinates of the corresponding point on the tomographic image. This is instead of the coordinates of the origin on the fundus image matching the origin on the tomographic image. As a result, as illustrated in FIGS. 4A to 4C, the coordinates in the above-mentioned three-dimensional coordinate system are converted to the display coordinate system in such a way that the arbitrary point 301 on the fundus image matches with the arbitrary point 301 on the tomographic image. In this orientation, the deviation is between the origin 0 of the fundus image and the center of the macula 302 on the tomographic image, which is labeled 303 in FIG. 4C. Those coordinate conversions are executed by the display control portion 113 And some other components serving as a unit that converts the coordinate system for displaying the tomographic image and the fundus image in association with each other on the basis of the positions of an arbitrary point and a point corresponding to the arbitrary point according to the present invention.

Figure 5A:
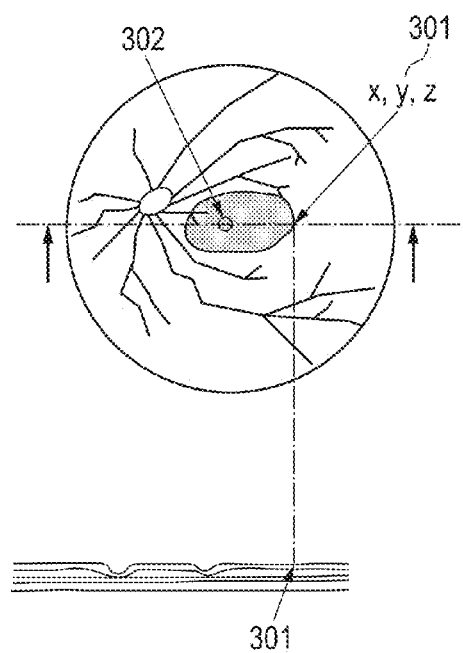
FIGS. 5A and 5B are diagrams exemplifying images to be displayed on a monitor according to the first embodiment.
Figure 5B:
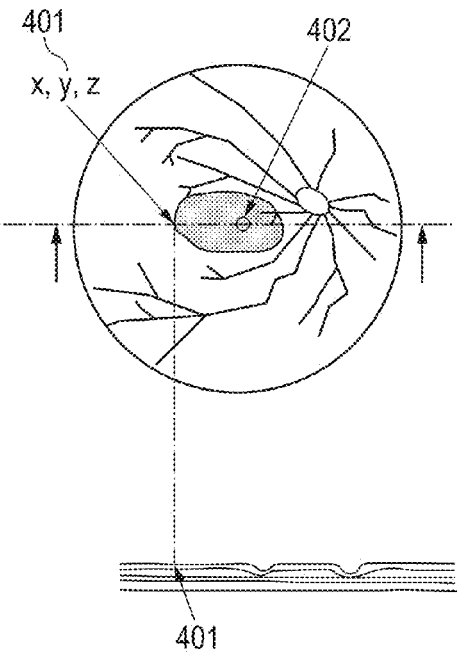

In Step S209, data acquired as the tomographic image using the display coordinate system calculated in Step S208 is displayed. In Step S209, the fundus image and the tomographic image are displayed on a display portion (not shown) as illustrated in, for example, FIGS. 5A and 5B. When both eyes are inspection targets in the above-mentioned flow, the display is provided so that both eyes are associated with each other and the designated arbitrary point or characteristic point on the fundus image is associated with an equivalent point on the tomographic image, as illustrated in FIGS. 5A and 5B.

FIGS. 3A to 3C and FIGS. 4A to 4C illustrate examples of an aging-related macular degenerative fundus image and tomographic image. According to the present invention, the base point for matching a tomographic image with a fundus image can be changed in accordance with a region of interest (e.g., suspected lesion) so that diagnosis of a variety of diseases can be supported, and prompt diagnosis can be achieved. Because the thickness of a retina around a macula can be measured accurately according to the present invention, deviation from the fundus image is reduced by preparing a high-definition thickness map. FIGS. 5A and 5B illustrate an example in which the fundus images and tomographic images of both eyes of a person to be inspected having age-related macular degenerative disease of the eyes illustrated in FIGS. 3A to 3C, for example, are displayed on the monitor 114. In this embodiment, with regard to the images of both eyes acquired by the program flow illustrated in FIG. 2, macula portions 302 and 402 and arbitrary points 301 and 401 of the left and right eyes are aligned linearly and disposed to be displayed symmetrically as shown in FIGS. 5A and 5B. The operation, such as arrangement of the images of both eyes, originated from this display is carried out by the display control portion 113 According to this embodiment, even when both eyes are displayed, the images can be displayed with designated points and tomographic images being associated with each other and characteristic points of the right and left eyes being associated with each other at the time of analyzing the thickness of a retina, thus achieving easy comparison of the eyes and quick diagnosis.

Figure 6A:
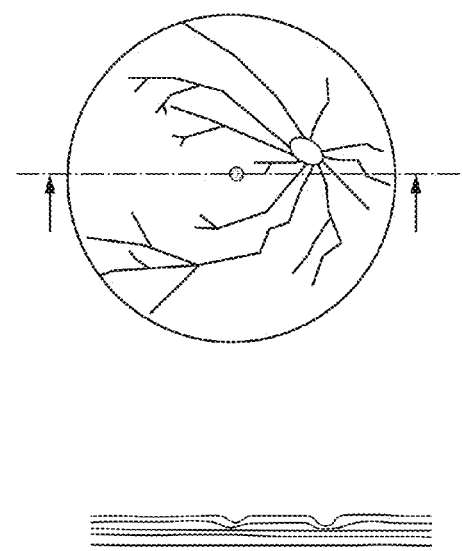
FIGS. 6A and 6B are diagrams illustrating an example in which a normal eye is displayed to be juxtaposed with an eye to be inspected at the time of displaying the eye to be inspected.
Figure 6B:
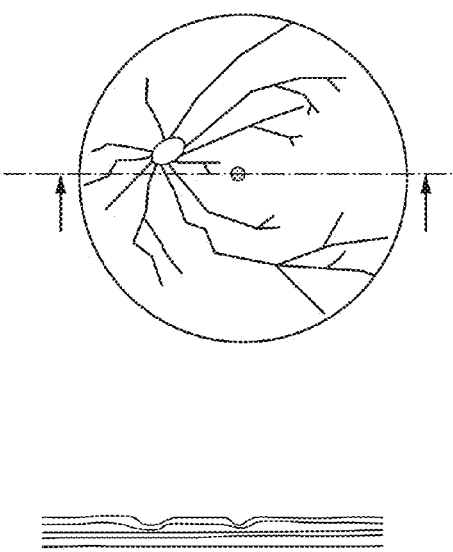

There is a case where at the time of displaying fundus images and tomographic images, for example, multiple images of an eye to be inspected and multiple images of a normal eye to be compared therewith are displayed in alignment. In this case, in consideration of ease of inspection, it is preferred that any one of the images of the eye to be inspected and the images of the normal eye be displayed in reverse. The case of presenting such mirror-reversed display of an image is described referring to FIGS. 6A and 6B and FIGS. 7A and 7B. FIG. 7A illustrates an example in which a fundus image and a tomographic image of FIG. 6A are displayed as mirror-reversed images. FIG. 6A illustrates the fundus image and tomographic image of the normal right eye. This displayed data represents normal eye data stored in the data server 102 in FIG. 1 for diagnosis of glaucoma. FIGS. 6B and 7B illustrate the left eyes of the same person who is suspected to have glaucoma and is different from the person in FIG. 6A. The displays of FIGS. 6A and 6B, which are compared with each other with the left and right eyes, are not ideal for comparing like-for-like in the eyes. To address this, when a command to mirror-reverse the display of the normal eye is output via a user interface (not shown), the display of FIG. 6A is mirror-reversed as illustrated in FIG. 7A. With the displays of FIGS. 7A and 7B presented, the images can be compared as if the fundus images and the tomographic images are displayed on the same side, thereby facilitating comparison of the fundus image and tomographic image which show suspected glaucoma. This results in efficient diagnosis. In addition, data on just one normal eye is sufficient as normal eye data (i.e. both left and right normal eyes do not need to be stored, as one can be compared with both when it is mirror-reversible) so that the capacity of the data server 102 in FIG. 1 can be saved. The actual operation is carried out in response to a command to mirror-reverse the display, which is output to the display control portion 111 from the operation portion 115 And the display control portion 111 electronically reverses the display of the normal eye in response to the command. Although a normal eye is reversed according to this embodiment, an eye to be inspected may be reversed. Further, it is preferred that multiple eyes on one side (eyes to be inspected) be displayed, and the images of the normal eyes respectively corresponding to the eyes on one side be displayed simultaneously in a juxtaposed manner. The display control portion 111 serves as a means or unit for displaying multiple eyes on one side in mirror-reversed fashion for comparison according to the present invention.

Second Embodiment

Figure 8:
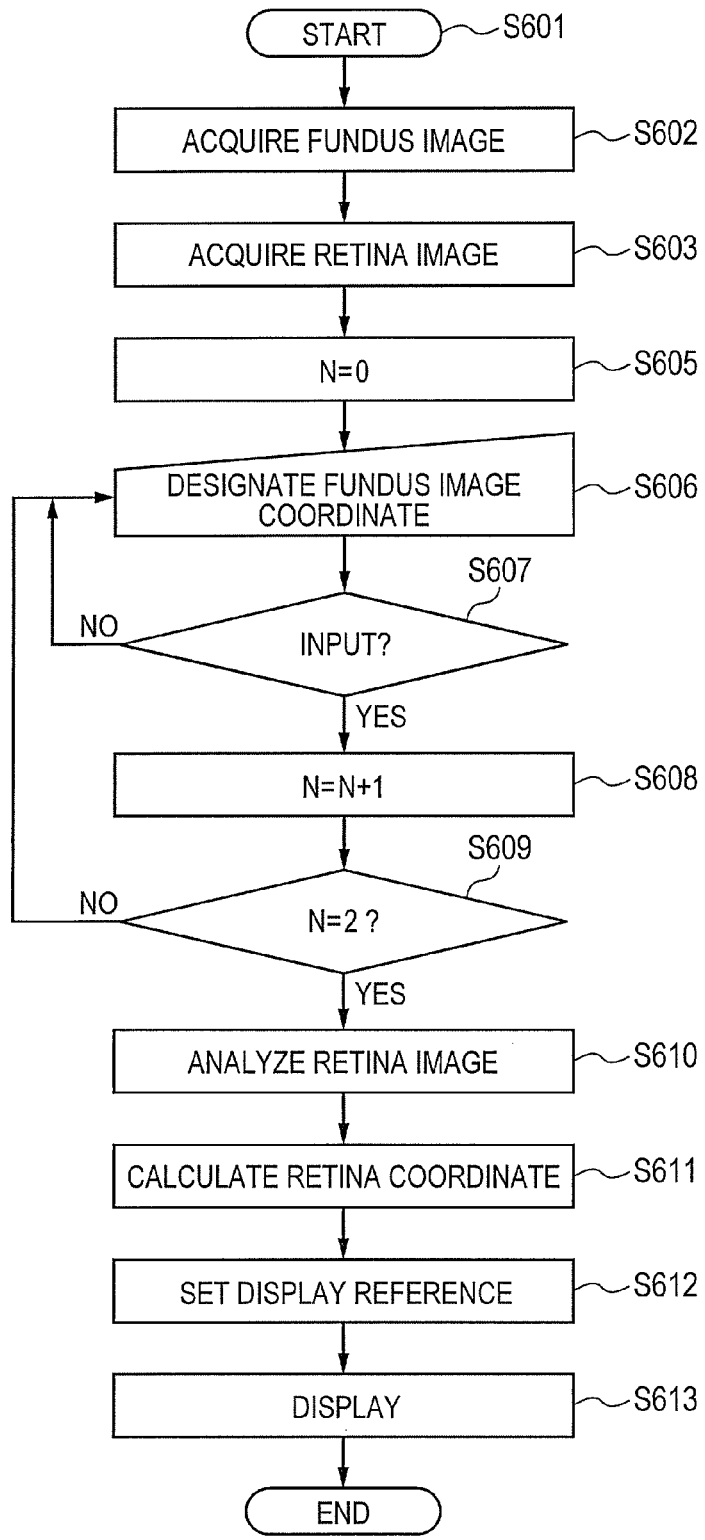
FIG. 8 is a flowchart illustrating the program flow of image processing according to a second embodiment of the present invention.

In the following description of a second embodiment of the present invention, two arbitrary points are designated to illustrate a correspondence between a tomographic image and a fundus image. Because a block diagram illustrating the configuration of the apparatus is the same as that of the first embodiment, its description is omitted herein. The second embodiment differs from the first embodiment in the flow of the image processing program as illustrated in FIG. 8. The program flow is described hereinafter.

Step S601 is the start of the flow of the image processing program. In Step S602, the fundus/tomographic image photographing device 101 acquires the tomographic image of an eye to be inspected. Then, the two-dimensional XY coordinate system is calculated with a macula portion 703 of FIGS. 9A and 9B taken as the origin 0, and the two-dimensional XY coordinate system is sent to the memory portion 106 with this origin as the origin of the reference coordinates. Those processes are executed by the fundus image acquiring portion 107.

In Step S603, the fundus/tomographic image photographing device 101 acquires the tomographic image of the eye to be inspected. Because the operations that are executed in Steps S602 and S603 are identical to those executed in Steps S202 and S203 according to the first embodiment described above, their detailed descriptions are omitted.

In next Step S605, 0 is given as the value for a counter variable N. In Step S606, the coordinates of a characteristic point of a portion to be diagnosed on the fundus image are designated as an arbitrary point. In Step S607, it is determined whether or not the coordinates of this arbitrary point are input. Because the processes to be executed in Steps S606 and S609 Are the same as those in Steps S204 and S205 according to the first embodiment described above, their descriptions are omitted herein.

When it is determined in Step S607 that the coordinates of this arbitrary point are input, the flow proceeds to Step S608 to increment the counter variable N by "1". The sequence of processes of Steps S606 to S609 is repeated until the counter variable N becomes "2" in Step S609. When the counter variable N becomes "2", the flow proceeds to Step S610.

Figures 9A, 9B, 9C:
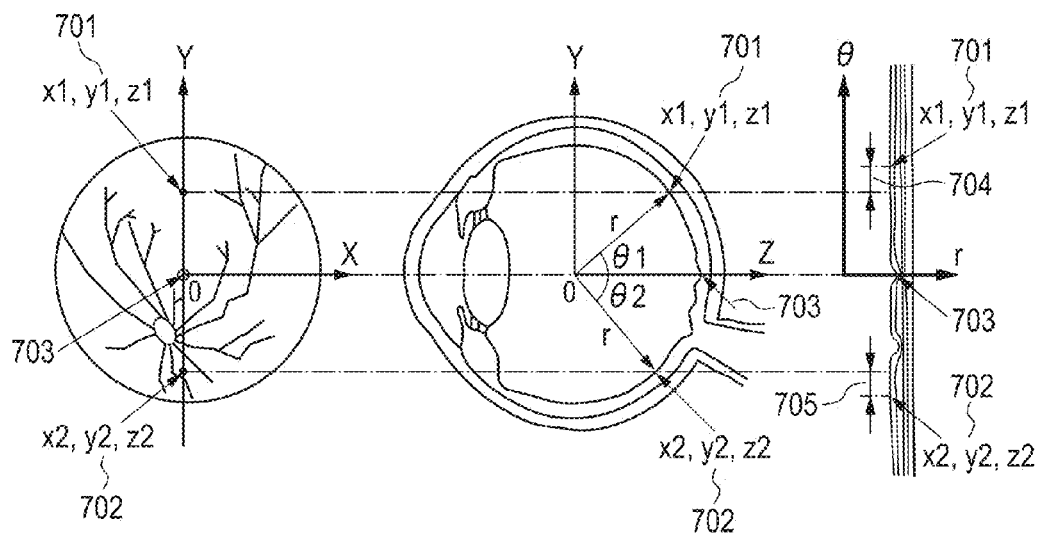
FIGS. 9A, 9B and 9C are diagrams illustrating an operation for retina image analysis and calculation of retina coordinates which are carried out in the image processing according to the second embodiment.

A process which is executed in Step S610 is described referring to FIGS. 9A to 9C. FIG. 9A illustrates the fundus image of an eye to be inspected, FIG. 9B illustrates the cross section of the eyeball of the eye to be inspected, and FIG. 9C illustrates the tomographic image of the eye to be inspected. A first arbitrary point 701 has its coordinates (x1, y1, z1) designated as a characteristic point which represents a portion to be diagnosed in the XY coordinate system set for the fundus image. A second arbitrary point 702 has its coordinates (x2, y2, z2) designated as a characteristic point different from the first arbitrary point 701. The macula portion 703 is designated as the origin or the reference coordinates in the XY coordinate system. FIG. 9B illustrates the coordinates of those first arbitrary point 701 and second arbitrary point 702 on the fundus as points projected on the retina by the same reference numerals. FIG. 9C is a diagram illustrating an expanded tomographic image having the macula portion 703 on the fundus image and the macula portion 703 on the eyeball in association with each other.

In Step S610, the radius r of the eyeball and the center point O in the eyeball in the cross-sectional view illustrated in FIG. 9B are determined, and then correspondence between the above-mentioned origin and the center point in the three-dimensional coordinates set for the tomographic image is made. Further, the reference coordinates (x,y,z) which are matched with the XY coordinates set for the fundus image are calculated. In addition, the coordinates (x1,y1,z1) of the first arbitrary point 701 and the coordinates (x2,y2,z2) of the second arbitrary point 702 in the reference coordinates are calculated.

In Step S613A first deviation amount 704 between the first arbitrary point 701 on the tomographic image and the first arbitrary point 701 on the fundus image, and a second deviation amount 705 between the second arbitrary point 702 on the tomographic image and the second arbitrary point 702 on the fundus image are calculated when a correspondence is found between the origin on the fundus image and the origin in the reference coordinates on the tomographic image. The first deviation amount 704 is determined by first considering the tomographic image in FIG. 9C and calculating a "retina expansion distance" (r$\theta$1) which is the distance from the origin line in the three-dimensional coordinates to the first designated point (x1,y1,z1) 701, and then considering the fundus image in FIG. 9A and subtracting the coordinate value y1 in the Y direction in the XY coordinate system from the retina expansion distance r$\theta$1. Similarly, the second deviation amount 705 is determined as a distance obtained by calculating a retina expansion distance (r$\theta$2) to the second designated point (x2,y2,z2) and then subtracting the coordinate value y2 in the Y direction from the retina expansion distance r$\theta$2.

Figures 10A, 10B, 10C:
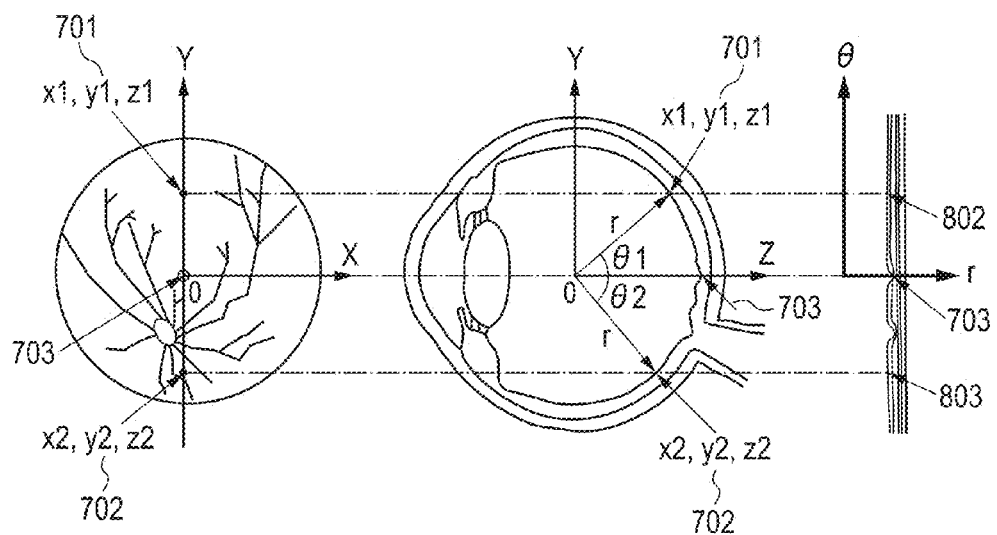
FIGS. 10A, 10B and 10C are diagrams illustrating an operation for the calculation of retina coordinates and setting of a display reference which are carried out in the image processing according to the second embodiment.

In Step S612, the coordinates of the tomographic image are converted to the display coordinate system on the basis of the first and second deviation amounts 704 and 705 calculated in Step S611 in such a way that correspondence is made between first and second designated points 701 and 702 on the tomographic image and the first and second arbitrary points 701 and 702 on the fundus image. The operation in this Step S612 is described referring to FIGS. 10A to 10C. FIGS. 10A and 10B respectively correspond to FIGS. 9A and 9B, and FIG. 10C illustrates a tomographic image on the display coordinate system. A first point 802 in FIG. 10C is displayed as a position corresponding to the first arbitrary point 701 (x1,y1,z1) of FIG. 9C. A second point 803 is displayed as a position corresponding to the second arbitrary point 702 (x2,y2,z2). When the display coordinate system used for displaying the tomographic image in FIG. 9C is changed to the display coordinate system used for displaying the tomographic image in FIG. 10C, it is sufficient simply that the $\theta$ coordinate system of the tomographic image in FIG. 9B be multiplied by the following coefficients for the conversion.

coefficient of range 0≤y≤y1: y1/r$\theta$1
coefficient of range y2≤y<0: y2/r$\theta$2

Figure 11A:
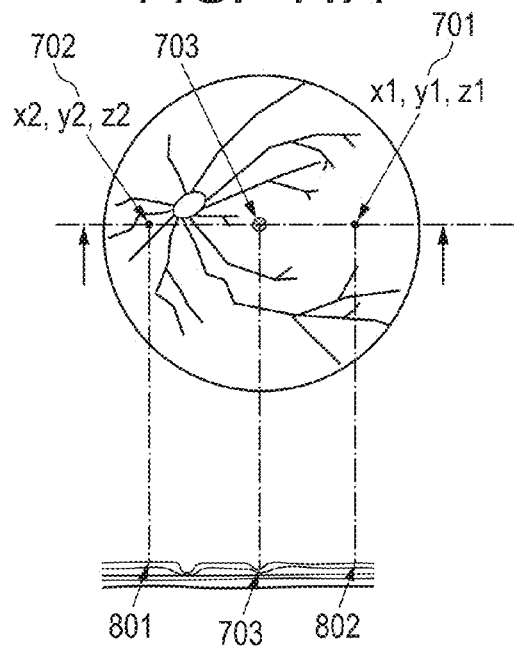
FIGS. 11A and 11B are diagrams exemplifying images to be displayed on a monitor according to the second embodiment.
Figure 11B:
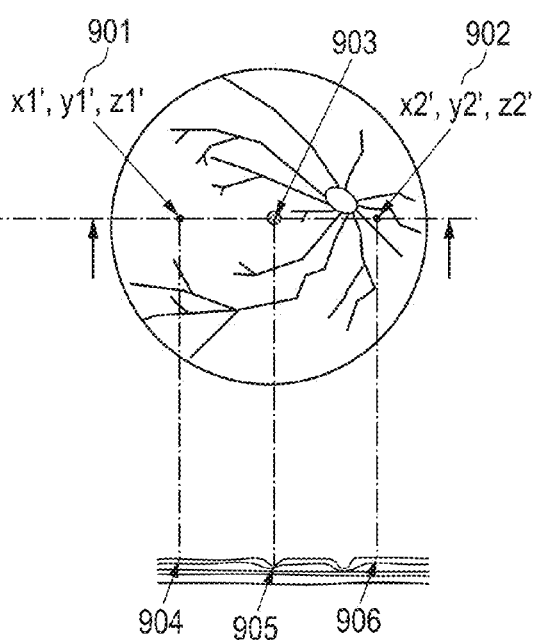

While the operation from Step S602 to S612 has been described of the case of acquiring the image of the left eye, similar processing is performed for the image of the right eye at the same time. In Step S613, the data converted in Step S612 is displayed on the monitor 116 Actually, the tomographic images and fundus images of both eyes are displayed as exemplified in FIGS. 11A and 11B. More specifically, with regard to the images of both eyes acquired by the program flow illustrated in FIG. 8, the macula portion 703, the first arbitrary point 701, and the second arbitrary point 702 of the left eye, and a macula portion 903, a first arbitrary point 901, and a second arbitrary point 902 of the right eye are arranged so as to be aligned in a line and displayed symmetrically. The operation on the arrangement and the like of the images of both eyes involving the display is executed by the display control portion 113 According to the second embodiment, as illustrated in the figures, the tomographic images can be displayed so as not to achieve pin-point matching as exemplified in the first embodiment, but to ensure that the range from the macula portion of the reference point (above-mentioned origin) to the coordinate value of y1 or y2 corresponds to the respective portion of the fundus image. FIG. 11A shows a tomographic image below the left eye with the macula 703 aligned with the macula 703 of the fundus image, a position 802 corresponding to the arbitrary point 701 and the position 801 corresponding to the arbitrary point 702 of the fundus image. FIG. 11B similarly shows the tomographic image below the fundus image with a macula portion 905 corresponding to the macula portion 903 of the fundus image and positions 906 and 904 corresponding to fundus positions 902 and 901 respectively.

According to the second embodiment, as described above, the state of the fundus and the thickness of the retina in a specific arbitrary range can be associated with each other so as to enable asymmetry analysis of the thicknesses of the retina around a macula portion and a papilla, which is effective in diagnosing glaucoma, macular degeneration, etc. According to the second embodiment, the base point for matching a tomographic image with a fundus image can be changed in accordance with a region of interest (e.g., suspected lesion) so that diagnosis of a variety of diseases can be supported, and prompt diagnosis can be achieved.

Although the description of the second embodiment has been given of the case where two arbitrary points are designated, the present invention is not limited thereto, and the second embodiment can be applied to a case where three or more arbitrary points are designated.

Third Embodiment

Figure 12:
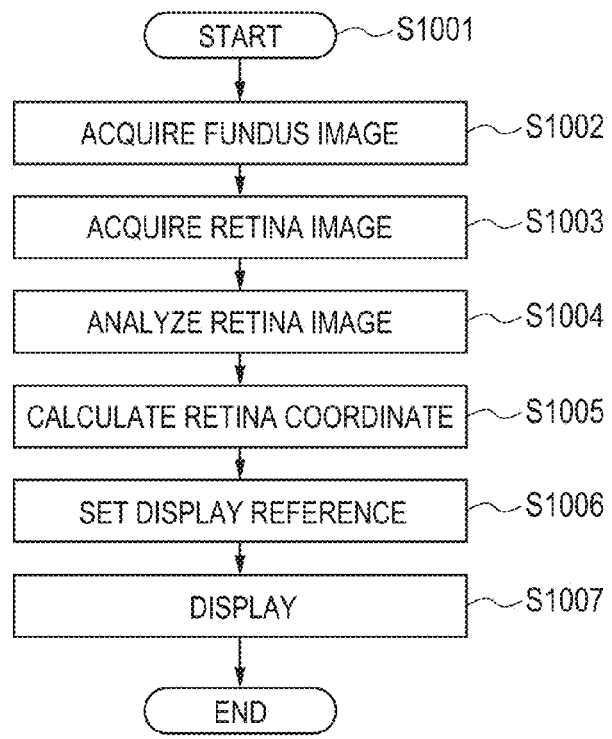
FIG. 12 is a flowchart illustrating the program flow of image processing according to a third embodiment of the present invention.

In a third embodiment of the present invention, the coordinates of arbitrary points are extracted as characteristic points on the fundus, and correspondence between a tomographic image and a fundus image is made using these arbitrary points. Because a block diagram illustrating the configuration of the apparatus is the same as that of FIG. 1 in the first embodiment, its description is omitted herein. The third embodiment differs from the first embodiment in the program flow as illustrated in FIG. 12. The program flow is described hereinafter.

Step S1001 is the start of the program flow which is carried out by the image processing portion 103 and other involved components. In Step S1002, the fundus/tomographic image photographing device 101 acquires the tomographic image of an eye to be inspected. In Step S1003, arbitrary points are extracted from the fundus image acquired in Step S1002, a vector is calculated through an operation to be described later, and an XY coordinate system is established on the fundus image of the eye to be inspected.

The specific procedures of the above-mentioned operation are described referring to FIGS. 13A to 13C. According to this embodiment, a first arbitrary point 1101 represents a macula portion, and a second arbitrary point 1102 represents a papilla portion. First, a vector (hereinafter referred to as "Y-directional vector") extending from the second arbitrary point (papilla portion) 1102 in the direction of the first arbitrary point (macula portion) 1101 is defined. Next, a directional vector extending perpendicularly to the Y-directional vector from the first characteristic point 1101 is defined as "X-directional vector". Then, an XY reference coordinate system with the first arbitrary point 1101 as the origin is established. Information on the established reference coordinate system is sent to the memory portion 106 by the fundus image acquiring portion 107. That is, according to the third embodiment, the operation portion 113 serves as a means or unit for designating two arbitrary points on the fundus image, and the fundus image acquiring portion 107 serves as a means or unit for calculating a vector formed between the two arbitrary points. Further, the fundus image acquiring portion 107 serves as a means or unit for calculating a coordinate system with the vector being set as one axis and one of the two arbitrary points being set as the origin.

On a fundus image in FIG. 13A, the coordinates of the first arbitrary point 1101 are set as (x1,y1), and the coordinates of the second arbitrary point 1102 are set as (x2,y2). In next Step S1003, the fundus/tomographic image photographing device 101 acquires the tomographic image of the eye to be inspected. In Step S1004, the radius r of the eyeball is calculated from the tomographic image acquired in Step S1003, and the Z-directional coordinates illustrated in FIG. 13B are also calculated from the coordinates of the first arbitrary point 1101 and the second arbitrary point 1102 calculated in Step S1002. Through the procedures, the coordinates of the first arbitrary point 1101 corresponding to the macula portion and the second arbitrary point 1102 corresponding to the papilla portion in the three-dimensional coordinate system are calculated.

In Step S1005, a deviation amount 1103 is calculated between the coordinates of the second arbitrary point 1102 on the fundus and the coordinates of the position of the second arbitrary point 1102 in the three-dimensional coordinate system of the cross section of the eye to be inspected when expanded as a tomographic image. To determine the deviation amount 1103, the retina expansion distance (rθ1) from the coordinates of the first arbitrary point 1101 in the three-dimensional coordinate system to the coordinates of the second arbitrary point 1102 in the three-dimensional coordinate system is calculated. The deviation amount 1103 is determined as the distance obtained by subtracting y2, which is the Y-directional coordinate value of the second arbitrary point 1102 in the XY coordinate system on the fundus image, from the retina expansion distance (rθ1). The above-mentioned operation is executed by the retina image analysis portion 110 and some components serving as a means or unit for matching the origin of the coordinate system with the corresponding arbitrary point on a tomographic image and a means or unit for calculating the deviation amount between the position of an arbitrary point on the fundus image which is not subjected to matching, and the position of a corresponding arbitrary point on the tomographic image according to the third embodiment.

In Step S1006, the coordinates of the tomographic image are converted to the display coordinate system on the basis of the deviation amount 1103 calculated in Step S1005 so that with the macula portion or the first arbitrary point being the base point of the coordinates, correspondence is made between the second arbitrary point 1102 on the fundus image in FIG. 13A and the second arbitrary point 1102 on the expanded tomographic image. This operation is described referring to FIGS. 14A to 14C. The coordinates of the second arbitrary point 1102 represent a position corresponding to (x2,y2,z2), and the coordinates of the first arbitrary point 1101 represent a position corresponding to (x1,y1,z1). To change the display coordinate system to make a correspondence between those corresponding arbitrary points in the XY coordinate system, it is sufficient simply that the θ coordinate system of a tomographic image illustrated in FIG. 14B be multiplied by the following coefficient for the conversion.

coefficient of range y2≤y≤y1: y1/rθ1

The above-mentioned operation is executed by the display control portion 113 And some other components serving as a means or unit for converting a tomographic image on the basis of the deviation amount so that two arbitrary points on a fundus image match with the two corresponding points on the tomographic image corresponding.

Figure 15A:
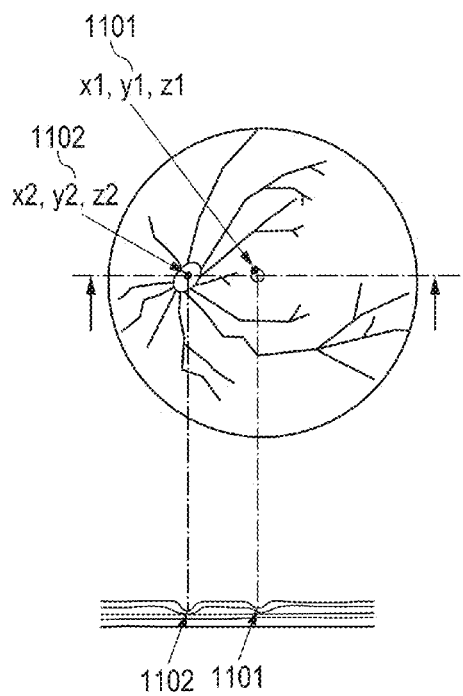
FIGS. 15A and 15B are diagrams exemplifying images to be displayed on a monitor according to the third embodiment.
Figure 15B:
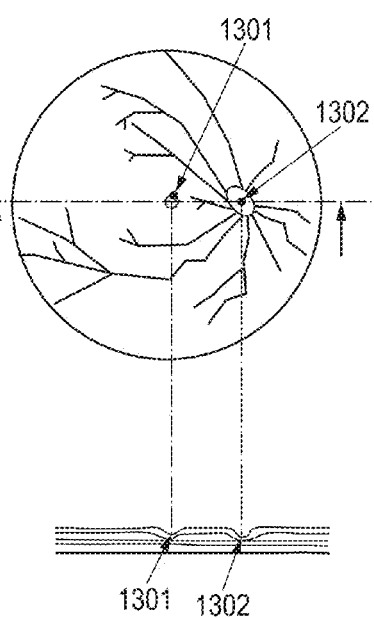
Figure 16A:
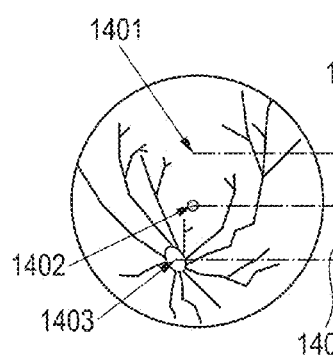
FIGS. 16A, 16B and 16C are diagrams schematically illustrating the relation between a fundus image and a retina tomographic image which are acquired according to the related art.
Figure 16B:
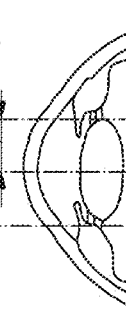
Figure 16C:
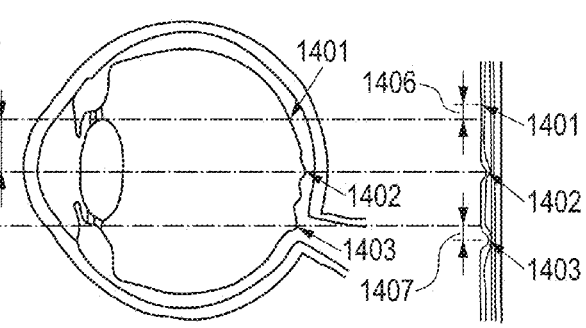

Although the description of the operation from Step S1002 to Step S1006 has been given of the case of acquiring the image of a left eye, similar processing is performed on the image of a right eye at the same time. In Step S1007, the data converted in Step S1006 is displayed on the monitor 116 Actually, as exemplified in FIGS. 15A and 15B, tomographic images and fundus images of both eyes may be displayed. More specifically, with regard to the images of both eyes acquired by the program flow illustrated in FIG. 12, the macula portion 1101 corresponding to the first arbitrary point, and the papilla portion 1102 corresponding to the second arbitrary point of the left eye, and the macula portion 1301 corresponding to the first arbitrary point, and the papilla portion 1302 corresponding to the second arbitrary point of the right eye are arranged so as to be aligned in a line and displayed symmetrically. The display of the fundus image and the tomographic image of the eye to be inspected in this manner provides correspondence between the fundus and the retina thicknesses of the macula portion 1101 and the papilla portion 1102. The retina thicknesses of the macula portion 1101 and the papilla portion 1102 are effective in diagnosing initial glaucoma. According to the third embodiment, the base point for matching a tomographic image with a fundus image can be changed in accordance with a region of interest (e.g., suspected lesion) so that diagnosis of a variety of diseases can be supported, and prompt diagnosis can be achieved.

Other Embodiments

The present invention is not limited to the above-mentioned embodiments, and may be modified and changed in various other forms without departing from the scope of the present invention. For example, the above-mentioned embodiments have described the case where an object to be inspected is an eye, but the present invention can be applied to other objects to be inspected than the eye, such as skin or another organ.

Further, in a case where the fundus image and the tomographic image of a left eye or a right eye are displayed as illustrated in FIGS. 5A and 5B on a display portion (not shown) as in the above-mentioned embodiments, when an inspector moves the designated point 301 with an operation unit such as a mouse, for example, the display control portion 113 Changes a tomographic image to be displayed on the display portion in accordance with the movement of the designated point 301. Specifically, when the designated point 301 is moved by dragging or rotation of a mouse wheel, the operation of Steps S206 to S209 of FIG. 2 is performed on the basis of the moved designated point 301. In other words, movement of the designated point 301 causes the display control portion 111 to sequentially display tomographic images at the positions of the moved designated point 301 on the display portion. The same is true of the case where the designated point 401 is moved.

In this manner, the tomographic images can be displayed successively in addition to the effects provided by the above-mentioned embodiments, thus ensuring faster diagnosis.

The example of sequentially displaying tomographic images can be applied to a case where the fundus images and tomographic images of left and right eyes are displayed. That is, in the case where the fundus images and tomographic images of left and right eyes are displayed on the display portion as illustrated in FIGS. 5A and 5B, the designated point 401 may be moved in synchronism with the movement of the designated point 301, and tomographic images corresponding to the positions of the designated points 301 and 401 may be sequentially displayed on the display portion by the display control portion 111. In this manner, the designated points 301 and 401 indicate the same position on the fundus image, and the tomographic images of the left and right eyes at this same position are displayed. Note that, the word "same" is a conceptual word including the case of exact matching and the case of substantial matching. Further, the designated point 401 is moved in synchronism with the movement of the designated point 301, and hence the image processing portion 103 needs to grasp, for example, the correspondence between the fundus image of the left eye and the fundus image of the right eye beforehand. The tomographic images of the same eye on different dates and times, not the tomographic images of both the left and right eyes, may be displayed for time-variant observation of the same eye.

This modification can ensure comparison of the tomographic images of the left and right eyes at the same position in addition to the effects provided by the above-mentioned embodiments, thus ensuring faster diagnosis.

The following describes an example of a mode wherein, during a mode of displaying left and right eyes simultaneously, when a designated position of a tomographic image of one eye is moved, a designated position of the tomographic image of the other eye is also moved in response to the movement of the tomographic image position of the first eye. Although the following description of this embodiment is given regarding a case where a designation line in a fundus image is moved instead of the aforementioned designated points 301 and 401, the mode concerning the designated points or the designation line is not limited to this example.

Figure 17:
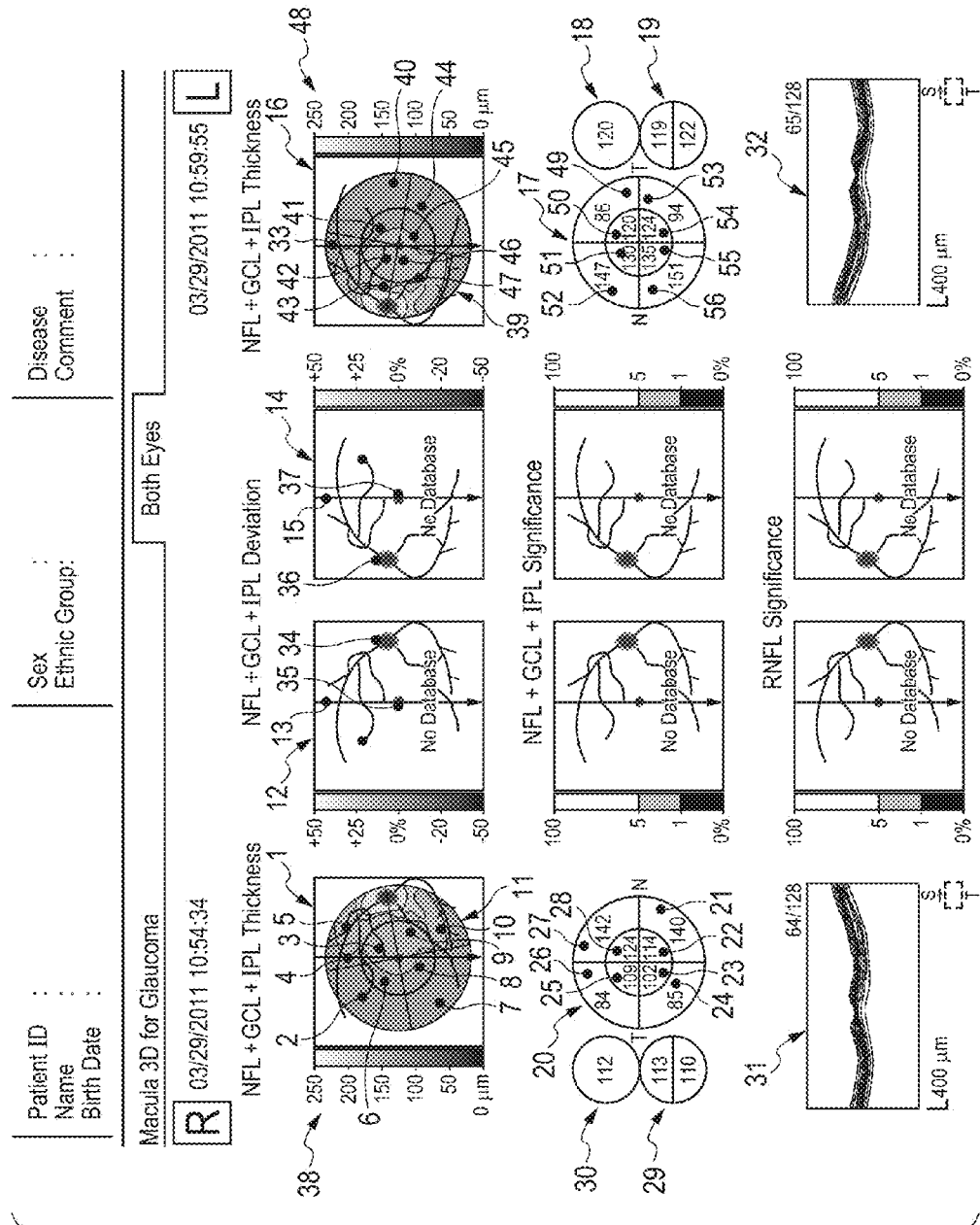
FIG. 17 is a diagram illustrating an example of a monitor screen when left and right eyes are displayed simultaneously according to another embodiment of the present invention.

FIG. 17 illustrates a case where the fundus images of left and right eyes, thickness maps thereof, and the like are displayed on the monitor 114 simultaneously. More specifically, the following describes an embodiment of comparison of the cross-sections of both left and right eyes with each other. This cross-section comparison involves a map of the total thickness of a nerve fiber layer (NFL), a ganglion cell layer (GCL), and an inner plexiform layer (IPL).

FIG. 17 illustrates the screen display of the monitor 114 and shows a fundus image 12 of the right eye, a papilla portion 34 of the right eye, a macula portion 35 of the right eye, a fundus image 14 of the left eye, a papilla portion 36 of the left eye, and a macula portion 37 of the left eye.

A map 1 represents a total thickness map of NFL, GCL, and IPL of the right eye. The total thickness map of NFL, GCL, and IPL is hereinafter called "NFL+GCL+IPL thickness map". A chart 11 represents the NFL+GCL+IPL thickness map chart of the right eye, which is quadrisected within two concentric circles by two lines passing through the centers of the circles. The lines cross each other at right angles. The circular center of the NFL+GCL+IPL thickness map chart 11 is arranged at the center of the macula portion. One of the two lines quadrisecting the two concentric circles is arranged to overlap the line that passes through the centers of the macula portion 35 and the papilla portion 34. Accordingly, the NFL+GCL+IPL thickness map chart 11 is segmented into eight regions 2, 5, 10, 7, 8, 9, 3, and 6. A reference gray scale bar 38 expresses the NFL+GCL+IPL thickness in gray scale. The thicknesses from 0 μm to 250 μm are expressed in the gray scale. The NFL+GCL+IPL thickness in the NFL+GCL+IPL thickness map chart 11 is displayed in gray scale by the reference gray scale bar. A portion 20 shows the average value of the NFL+GCL+IPL thickness of each of the eight segmented regions of the NFL+GCL+IPL thickness map chart. A region 26 corresponds to the region 2. A region 27 corresponds to the region 5. A region 21 corresponds to the region 10. A region 24 corresponds to the region 7. A region 25 corresponds to the region 6. A region 28 corresponds to the region 3. A region 22 corresponds to the region 9. A region 23 corresponds to the region 8.

A portion 29 shows the average values of the NFL+GCL+IPL thicknesses of the regions 25, 26, 27 and 28 in its top half; and the regions 21, 22, 23, and 24 in its bottom half. A portion 30 shows the average value of the NFL+GCL+IPL thicknesses of all of the regions 25, 26, 27, 28, 21, 22, 23, and 24.

A human eye has symmetry at a line passing through the center of the macula portion and the center of the papilla portion. A T-N horizontal line of the portion representing the NFL+GCL+IPL thickness average value corresponds to the line passing through the center of the macula portion and the center of the papilla portion. It is possible to diagnose whether the right eye has a disease or not by checking the symmetry of the eye on this map.

An arrow 13 indicates the position of a tomographic image 31 of the right eye on the fundus, and corresponds to the above-mentioned designation line. The arrow 13 is the same as an arrow 4 in the NFL+GCL+IPL Thickness chart. The position of each of the arrow 13 and the arrow 4 can be shifted by the pointing device (not shown). When one of the arrows 13 and 4 is moved with the pointing device, the other cross-sectional arrow is moved to the same position.

A map 16 represents the NFL+GCL+IPL thickness map of the left eye. A chart 39 represents the NFL+GCL+IPL thickness map chart of the left eye, which is quadrisected in two concentric circles by two lines passing through the centers of the circles. The lines cross each other at right angles. The circular center of the NFL+GCL+IPL thickness map chart 39 is arranged at the center of the macula portion. One of the two lines quadrisecting the two concentric circles is arranged to overlap the line that passes through the centers of the macula portion 37 and the papilla portion 36. Accordingly, the NFL+GCL+IPL thickness map chart 39 is segmented into eight regions 40, 41, 42, 43, 44, 45, 46, and 47. A reference gray scale bar 48 expresses the NFL+GCL+IPL thickness in gray scale. The thicknesses from 0 µm to 250 µm are expressed in the gray scale. The NFL+GCL+IPL thickness in the NFL+GCL+IPL thickness map chart 39 is displayed in gray scale by the reference gray scale bar 48. A portion 17 shows the average value of the NFL+GCL+IPL thickness of each of the eight segmented regions of the NFL+GCL+IPL thickness map chart 39. Regions 49, 50, 51, 52, 53, 54, 55 and 56 correspond to the regions 40, 41. 42, 43, 44, 45, 46 and 47 respectively.

A portion 19 shows the average values of the NFL+GCL+IPL thicknesses of the regions 49, 50, 51 and 52 in its top half; and the regions 53, 54, 55, and 56 in its bottom half.

A portion 18 shows the average value of the NFL+GCL+IPL thicknesses of all of the regions 49, 50, 51, 52, 53, 54, 55, and 56.

A human eye has symmetry at a line passing through the center of the macula portion and the center of the papilla portion. A T-N line of the portion 17 representing the NFL+GCL+IPL thickness average value corresponds to the line passing through the center of the macula portion and the center of the papilla portion. It is possible to diagnose whether the left eye has a disease or not by checking symmetry on this map.

An arrow 15 indicates the position of a tomographic image 32 of the left eye on the fundus. The arrow 15 and an arrow 33 are located at the same position on the fundus. The position of each of the arrow 15 and the arrow 33 can be shifted by the pointing device (not shown). When one of the arrows 15 and 33 is moved with the pointing device, the other cross-sectional arrow is moved to the same position. The above gives the individual descriptions of the left and right eyes.

It is known that both human eyes are anatomically mirror-symmetrical to each other. A disease which is not found by checking one eye may be diagnosed by comparing the left and right eyes, and hence it is effective to compare both left and right eyes with each other using the mirror symmetry of the left and right eyes to find a disease.

Figure 18:
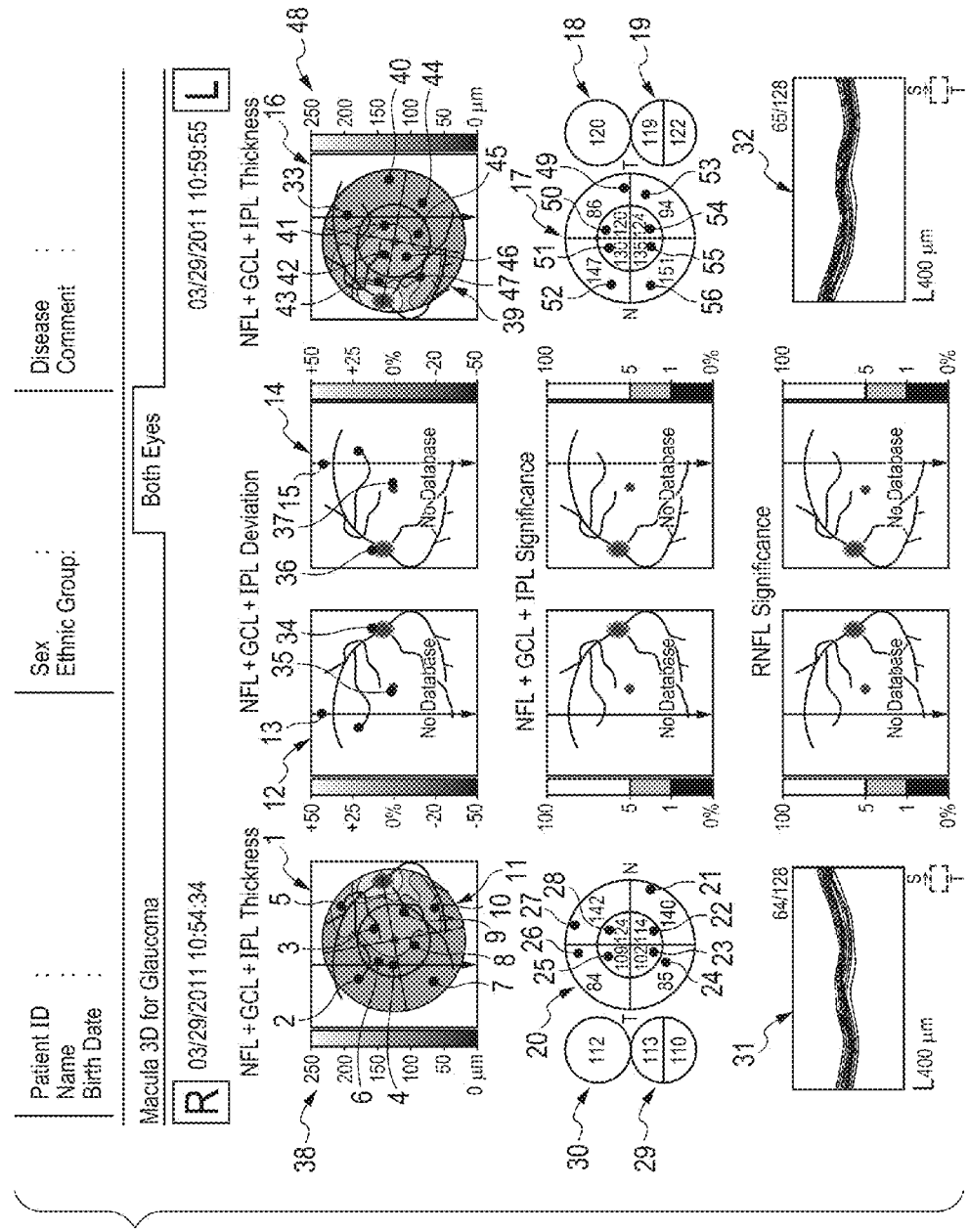
FIG. 18 is a diagram illustrating a display example when a designated position of a tomographic display is moved on the display illustrated in FIG. 17.

In the individual descriptions of the left and right eyes, the arrows 13, 4, 15, and 33 indicating the cross-sectional positions of tomographic images on the fundus are described. When each of the arrows is moved with the pointing device (not shown), the cross-sectional arrow of the other eye is moved to the mirror-symmetrical position described above. FIG. 18 shows a display on the monitor 114 after the arrow serving as the designation line is moved with the pointing device. For example, when the arrow 4 indicating the cross-sectional position of the right eye is moved left with respect to the macula portion with the pointing device as illustrated in FIG. 18, the arrows 15 and 33 for the left eye are also moved to positions mirror-symmetrical with respect to the right eye. As a result, the fundus cross sections of the left and right eyes at the mirror-symmetrical positions can be compared with each other.

Next, comparison of the NFL+GCL+IPL thickness map chart of the left eye with the NFL+GCL+IPL thickness map chart of the right eye is described. Because of the mirror symmetry of the left and right eyes, the NFL+GCL+IPL thickness map chart 11 of the right eye and the NFL+GCL+IPL thickness map chart 39 of the left eye correspond to each other as follows.

The regions 27, 26, 28 and 25 correspond to the regions 52, 49, 51 and 50 respectively. The regions 24, 21, and 22 correspond to the regions 53, 56, 54 and 55 respectively. The upper and lower parts of the portion 29 respectively correspond to the upper and lower parts of the portion 19. The portion 30 corresponds to the portion 18.

As described above, it is possible to diagnose whether or not an eye has a disease by comparing the tomographic images of both eyes at the same position with each other or comparing the NFL+GCL+IPL thickness map charts of both eyes with each other.

In addition to the exemplified case of displaying left and right eyes simultaneously, when the tomographic images of the left and right eyes at the same position on the fundus image are compared and coincidence is equal to or less than a predetermined threshold value, the tomographic images which provide the coincidence equal to or less than the predetermined threshold value can be left displayed by the display control portion 111 regardless of the movement of the designated point 301 or 401. Regarding the comparison of tomographic images, the entire tomographic images may be compared with each other, or the tomographic images near the positions corresponding to the designated points 301 and 401 may only be compared with each other. The display control portion 111 may perform highlighting such as marking on portions of tomographic images which provide coincidence equal to or less than the predetermined threshold value on the display portion so that an inspector can identify different portions in the tomographic images of the left and right eyes. Further, not only comparison between the left and right eyes, but also comparison between the tomographic images of the same eye may be performed for, for example, time-variant observation of the same eye.

This modification allows an inspector to easily understand the difference between the tomographic images of the left and right eyes at the same position in addition to the effects provided by the above-mentioned embodiments, thus ensuring faster diagnosis. Further, comparison of only the tomographic images near the positions corresponding to the designated points 301 and 401 can suppress the processing load on the image processing portion 103 so that the image processing portion 103 can perform quicker determination on the comparison results. Because a tomographic image at a position near a designated point is a comparison target, a portion in a tomographic image that an inspector desires to compare is included in the comparison target, thus preventing reduction in the quality of diagnosis.

Although the designated point 301 is moved with an operation unit such as a mouse, the present invention is not limited thereto and the designated point 301 may be automatically moved along a predetermined locus. In this case, the movement of the designated point 301 is started upon, for example, depression of a movement-start button. The same is true of the case where the designated point 401 is moved.

The second and third embodiments may be applied to the example of sequentially displaying tomographic images with multiple points being designated on a fundus image.

Further, the present invention can be realized by executing the process in which a system or an apparatus is provided with the software (program) that achieves the above-mentioned functions of the exemplary embodiments over a network or via various kinds of storage media, and the computer (or CPU, MPU, or the like) of the system or the apparatus reads and runs the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2012-013251, filed Jan. 25, 2012, and No. 2012-190603, filed Aug. 30, 2012, which are hereby incorporated by reference herein in their entirety.

What is claimed is:

1. An image processing apparatus, comprising:
a fundus image acquiring unit configured to acquire a fundus image of an eye to be inspected;
a designating unit configured to designate at least two arbitrary points on the fundus image;
a tomographic image acquiring unit configured to acquire a tomographic image of the eye to be inspected;
a deviation amount calculating unit configured to calculate a deviation amount between a distance between a first arbitrary point and a second arbitrary point of the at least two arbitrary points on the fundus image, and a distance, measured along a retina on the tomographic image, between a first point and a second point on the tomographic image, wherein the first point and the second point correspond to the first arbitrary point and the second arbitrary point respectively; and
a converting unit configured to convert the tomographic image on the basis of the deviation amount so that the first and second arbitrary points on the fundus image match with corresponding points on the tomographic image.

2. An image processing apparatus according to claim 1, further comprising a display unit configured to display a tomographic image and a fundus image of a left eye and a tomographic image and a fundus image of a right eye at positions on a display corresponding to relative respective orientations of the left eye and the right eye.

3. An image processing apparatus according to claim 1, further comprising a display unit configured to display a mirror-reversed image of an eye.

4. An image processing apparatus according to claim 1, further comprising a display unit configured to display a mirror-reversed image of a left or right eye alongside an image of a right or left eye respectively.

5. An image processing apparatus according to claim 1, further comprising a display unit configured to display at least a NFL+GCL+IPL thickness chart of the left and right eyes and superimposing thereon a marker indicating a position of a respective tomographic image, wherein, when a marker of a first of the left or right eye is moved in the NFL+GCL+IPL thickness chart, the display unit is configured to move automatically a marker of the second of the left or right eye to a corresponding position in the second eye.

6. An image processing apparatus according to claim 1, wherein a distance between the first point and the second point on the tomographic image is an expansion distance.

7. An image processing method comprising:
acquiring a fundus image of an eye to be inspected;
designating at least two arbitrary points on the fundus image;
acquiring a tomographic image of the eye to be inspected;
calculating a deviation amount between a distance between a first arbitrary point and a second arbitrary point of the at least two arbitrary points on the fundus image and a, measured along a retina on the tomographic image, distance between a first point and a second point on the tomographic image, wherein the first point and the second point correspond to the first arbitrary point and the second arbitrary point respectively; and
converting the tomographic image on the basis of the deviation amount so that the first and second arbitrary points on the fundus image match with the respective corresponding points on the tomographic image.

8. A non-transitory computer readable medium storing a program which, when run on a computer, causes the computer to execute the respective steps of the image processing method as set forth in claim 7.

9. An image processing apparatus, comprising:
a fundus image acquiring unit configured to acquire a fundus image of an eye to be inspected;
a designating unit configured to designate at least one arbitrary point on the fundus image;
a tomographic image acquiring unit configured to acquire a tomographic image of the eye to be inspected;
a deviation amount calculating unit configured to calculate a deviation amount between the arbitrary point and a point measured along a retina on the tomographic image which corresponds to the arbitrary point when a curvature of the tomographic image comes close to flat; and
a converting unit configured to convert the tomographic image on the basis of the deviation amount so that the arbitrary point on the fundus image matches with the point on the tomographic image.

10. An image processing apparatus, comprising:
a fundus image acquiring unit configured to acquire a fundus image of an eye to be inspected;
a designating unit configured to designate at least one arbitrary point on the fundus image;
a tomographic image acquiring unit configured to acquire a tomographic image of the eye to be inspected;
a deviation amount calculating unit configured to calculate a deviation amount between the arbitrary point and a point measured along a retina on the tomographic image which corresponds to the arbitrary point when a curvature of the tomographic image comes close to flat; and
a display control unit configured to cause a display unit to display the tomographic image and the fundus image on the basis of the deviation amount so that the arbitrary point on the fundus image matches with the point on the tomographic image.

11. An image processing apparatus according to claim 10, wherein the display control unit controls the display unit to display the tomographic image with the fundus image.

12. An image processing apparatus according to claim 10, wherein the display control unit controls the display unit to display the tomographic image and the fundus image so that the arbitrary point on the fundus image and the point on the tomographic image are arranged on one line.

13. An image processing apparatus according to claim 11, wherein the display control unit controls the display unit to display the tomographic image and the fundus image so that the arbitrary point on the fundus image and the point on the tomographic image are arranged on one line.

14. An image processing apparatus according to claim 10, wherein the display control unit controls the display unit to display the tomographic image two-dimensionally.

15. An image processing apparatus according to claim 11, wherein the display control unit controls the display unit to display the tomographic image two-dimensionally.

16. An image processing apparatus according to claim 12, wherein the display control unit controls the display unit to display the tomographic image two-dimensionally.

17. An image processing apparatus according to claim 13, wherein the display control unit controls the display unit to display the tomographic image two-dimensionally.

\* \* \* \* \*